(12) United States Patent
Zheng et al.

(10) Patent No.: US 11,982,664 B1
(45) Date of Patent: May 14, 2024

(54) TRUE THREE-DIMENSIONAL DYNAMIC AND STATIC COMBINATION SHEAR DEVICE UNDER HIGH- TEMPERATURE, HIGH PORE PRESSURE AND CHEMICAL COUPLING AND METHOD THEREFOR

(71) Applicant: GUANGXI UNIVERSITY, Nanning (CN)

(72) Inventors: Zhi Zheng, Nanning (CN); Guoshao Su, Nanning (CN); Cao Luo, Nanning (CN); Quan Jiang, Nanning (CN)

( * ) Notice: Subject to any disclaimer, the term of this patent is extended or adjusted under 35 U.S.C. 154(b) by 0 days.

(21) Appl. No.: 18/434,898

(22) Filed: Feb. 7, 2024

(30) Foreign Application Priority Data

Feb. 16, 2023 (CN) .......................... 202310121773.4

(51) Int. Cl.
| | | |
|---|---|---|
| G01N 33/24 | (2006.01) | |
| G01N 3/02 | (2006.01) | |
| G01N 3/24 | (2006.01) | |
| G01N 29/14 | (2006.01) | |

(52) U.S. Cl.
CPC .............. *G01N 33/24* (2013.01); *G01N 3/02* (2013.01); *G01N 3/24* (2013.01); *G01N 29/14* (2013.01)

(58) Field of Classification Search
CPC ............ G01N 33/24; G01N 3/02; G01N 3/24; G01N 29/14; G01N 15/082; G01N 3/04; G01N 3/00; G01N 1/08; G01N 3/22; G01N 3/12; G01N 15/0806; G01N 3/56; G01N 15/0826; G01N 33/222; G01N 3/30; G01N 15/14; G01N 15/08; G01N 3/06; G01N 19/00; G01N 3/303; G06F 30/23
See application file for complete search history.

(56) References Cited

FOREIGN PATENT DOCUMENTS

| AU | 2019101006 A4 | 10/2019 |
|---|---|---|
| CN | 2153053 Y | 1/1994 |
| CN | 103969107 A | 8/2014 |
| CN | 105927244 A | 9/2016 |
| CN | 106769539 A | 5/2017 |
| CN | 110658085 A | 1/2020 |
| CN | 111089781 A | 5/2020 |
| CN | 111238973 A | 6/2020 |
| CN | 112504847 A | 3/2021 |
| CN | 114279813 A | 4/2022 |

(Continued)

OTHER PUBLICATIONS

Jiankun Liu, "Dynamic characteristics of warm frozen soil under direct shear test-comparison with dynamic triaxial test", Soil Dynamics and Earthquake Engine, No. 30, Jun. 30, 2020.

(Continued)

*Primary Examiner* — Brandi N Hopkins

(57) ABSTRACT

The present application provides a true three-dimensional dynamic and static combination shear device under high-temperature, high pore pressure and chemical coupling and a method therefor, specifically designed for the rock indoor loading test technical field. The device includes a hydraulic system, a pore pressure coupling system, an annular frame, a frame base, a lateral horizontal support platform, a lateral floating frame, a normal dynamic and static combination loading cylinder, a lateral dynamic and static combination loading cylinder, a tangential hydrostatic loading cylinder, a tangential disturbance loading cylinder, a high-temperature box, and a true three-dimensional high-temperature, high pore pressure and chemical coupling shear box.

7 Claims, 5 Drawing Sheets

(56) References Cited

FOREIGN PATENT DOCUMENTS

| | | |
|---|---|---|
| CN | 114689441 A | 7/2022 |
| WO | 2018054041 A1 | 3/2018 |

OTHER PUBLICATIONS

Cui Guojian et al., "Development and application of multifunctional shear test apparatus for rock discontinuity under dynamic disturbance loading", Rock and Soil Mechanics, vol. 43 No. 6, Jun. 30, 2022.

TRUE THREE-DIMENSIONAL DYNAMIC AND STATIC COMBINATION SHEAR DEVICE UNDER HIGH- TEMPERATURE, HIGH PORE PRESSURE AND CHEMICAL COUPLING AND METHOD THEREFOR

CROSS-REFERENCE TO RELATED APPLICATIONS

This application claims priority to Chinese Patent Application No. 202310121773.4, titled "True Three-dimensional Dynamic and Static Combination Shear device Under High-temperature, High Pore Pressure and Chemical Coupling and Method Therefor", filed Feb. 16, 2023, the entire disclosure of which is incorporated herein by reference.

TECHNICAL FIELD

The present application relates to the technical field of rock indoor loading test, specifically a true three-dimensional dynamic and static combination shear device under high-temperature, high pore pressure and chemical coupling and a method therefor.

REARGROUND

Natural rock mass is pregnant with a large number of structural planes and fault zones, greatly changing the integrity of the rock mass, affecting the stability of the rock engineering, and the rock mass in the underground engineering is often in "three high and one disturbance" complex environment, such as the true three-dimensional high stress, high-temperature, high pore pressure, seepage stress. In acidic rain environments, water permeates through structural planes and causing erosion, which may accelerate deformation within the rock mass along structural planes and even leading to instability of rock mass. Consequently, collapses, deep fractures, rock explosions, and other engineering disasters can occur, which directly impeding construction processes and resulting in significant economic losses and threatening the safety of operators. Therefore, it is imperative to study the characteristics of the rock structural plane under the complex environment of multi-factor coupling.

Most existing rock shear devices are limited to conventional direct shear tests, which consider only tangential and normal stress while disregarding lateral stress. This setup does not accurately reflect the true triaxial stress conditions present in underground engineering rock structural planes. Currently, only a few rock shear devices incorporate shear functionality under true three-dimensional static conditions. However, there exists a significant gap in achieving true three-dimensional shear functionality for rocks subjected to both dynamic and static combined loads. Furthermore, there is a lack of rock shear devices capable of simultaneously applying dynamic and static combination loads in the tangential, normal, and lateral directions. The underground rock mass endure a complex environment characterized by high temperatures, high pore pressure and high stress. Additionally, the pore pressure water often carries acidic substances, continuously eroding the rock mass, thereby further compromising its integrity and mechanical properties. This erosion heightens the risk of instability and collapse in underground engineering projects. Consequently, rock shear devices should possess multifunctional capabilities to address the effects of these combined conditions. Currently, only a few rock shear devices can effectively conduct shear tests on rock structural planes under the combined influence of high temperatures, high pore pressure and chemical corrosion. Moreover, existing rock shear devices capable of applying pore pressure typically fall short of the high-pressure demands required for accurate testing.

In summary, the current rock shear devices exhibit several shortcomings. Firstly, they lack the capability to apply dynamic and static combination disturbance loads simultaneously in three directions—tangential, normal, and lateral. Currently, only a very limited number of rock shear devices possess the functionality for true three-dimensional static conditions. The development of devices and functional modules to apply disturbance loads in each direction based on true three-dimensional static conditions is still underway. Secondly, they fail to conduct shear tests on rock structural planes under multi-field coupling of "high-temperature—high-pressure—chemical corrosion". Most existing shear devices are conventional direct shear testing machines, which lack modules for high-temperature, high pore pressure, and chemical corrosion. While a small subset of shear devices accounts for temperature and pore pressure, they often fall short in achieving high pore pressure. Moreover, there has yet to be a device that considers the coupling effects of true three-dimensional dynamic and static stress fields, temperature, pore pressure, and chemical corrosion.

Consequently, there is an urgent need to develop a multifunctional rock structural plane shear device capable of simultaneously applying the multi-field coupling effects of dynamic and static combination loads, high-temperature, high pore pressure, and chemical corrosion in three-dimensional settings. This device will facilitate research on the true three-dimensional shear test of rock structural planes under the multi-field coupling effects of true three-dimensional dynamic and static combination disturbance loads, high-temperature conditions, high pore pressure, and chemical corrosion.

SUMMARY

This application addresses the limitations of current technology by presenting a true three-dimensional dynamic and static combination shear device under high-temperature, high pore pressure and chemical coupling. This device accurately replicates the shear damage process on rock structural planes induced by the combined effects of high-temperature, high pore pressure and chemical corrosion under true three-dimensional dynamic and static combination loading conditions.

To achieve the above purpose, the present application adopts the following technical solutions.

A true three-dimensional dynamic and static combination shear device under high-temperature, high pore pressure and chemical coupling, including:
  a hydraulic system, a pore pressure coupling system and a main body loading system;
  the main body loading system is connected to both the hydraulic system and the pore pressure coupling system and controlled by the hydraulic system to apply load to a sample; and
  the pore pressure coupling system is designed to supply water to a true three-dimensional high-temperature and high pore pressure shear box within the main body loading system, facilitating the completion of high-temperature, high pore pressure and chemical coupling for the sample.

In an embodiment, the main body loading system includes a frame base;
- a rear end of the frame base is provided with a lateral horizontal support platform, and a annular frame is fixed to an upper surface of the frame base through a bolt;
- a lower surface of an inner cavity of the annular frame is flush with an upper surface of the lateral horizontal support platform, and the lower surface of the inner cavity of the annular frame is provided with a slide rail extending to the lateral horizontal support platform;
- a lateral floating frame is provided on the slide rail through a slider, and a normal dynamic and static combination loading cylinder is fixed in a through-hole in an upper portion of the annular frame;
- a tangential disturbance loading cylinder is fixed in a through-hole in a front-side of the annular frame and a tangential hydrostatic loading cylinder is fixed in a through-hole in a rear-side of the annular frame;
- the lateral floating frame is of an U-type integrated frame, and a lateral dynamic and static combination loading cylinder is fixed in a through-hole in a right end of the lateral floating frame, and a left end of the lateral dynamic and static combination loading cylinder is connected to a lateral right indenter;
- a normal downward indenter is fixed in a vertical through-hole in a middle of the lateral floating frame, a lateral left indenter facing to the lateral right indenter is fixed to a left end of the lateral floating frame, and the high-temperature box is placed in the middle of the lateral floating frame, and the high-temperature box is provided with through-holes in a middle of six surfaces, such as a top, bottom, front, rear, left and right surface;
- the normal downward indenter is passed through a through-hole at a bottom of the high-temperature box, the lateral left indenter is passed through a through-hole at the left surface of the high-temperature box, and the lateral right indenter is passed through a through-hole at the right surface of the high-temperature box;
- a tangential rearward indenter of the tangential hydrostatic loading cylinder is passed through a through-hole at the front surface of the high-temperature box and a disturbance rod of the tangential disturbance loading cylinder is passed through a through-hole at the rear surface of the high-temperature box; and
- the true three-dimensional high-temperature and high pore pressure shear box is in the high-temperature box and is provided over the normal downward indenter inside the high-temperature box; and
- a normal upward indenter is passed through a through-hole at the top surface of the high-temperature box and then provided on a top of the true three-dimensional high-temperature and high pore pressure shear box.

In an embodiment, the normal dynamic and static combination loading cylinder and the lateral dynamic and static combination loading cylinder have same structures, and both include a dynamic and static front cylinder cover plate, and the dynamic and static front cylinder cover plate is fixed to a first cylinder barrel to form a hydrostatic cylinder cavity;
- a hydrostatic piston is provided inside the hydrostatic cylinder cavity to form a hydrostatic loading cylinder, a static force sensor is connected to a front end of the hydrostatic piston; a front end of a second cylinder barrel is extended into the first cylinder barrel and is fixed to the first cylinder barrel;
- a rear cylinder cover plate is fixed to a rear end of the second cylinder barrel to form a disturbance cylinder cavity; a front end of a disturbance piston is passed through the second cylinder barrel and an inside of the hydrostatic piston, and then provided in the second cylinder barrel to form a disturbance loading cylinder;
- a dynamic force sensor is connected to the front end of the disturbance piston; and
- a hydrostatic displacement sensor is provided on the dynamic and static front cylinder cover plate and a disturbance displacement sensor is provided on the disturbance piston.

In an embodiment, the tangential hydrostatic loading cylinder includes a hydrostatic front cylinder cover plate;
- the hydrostatic front cylinder cover plate is fixed to a hydrostatic cylinder barrel to form a tangential hydrostatic loading cylinder cavity;
- the hypertonic piston is provided in the tangential hydrostatic loading cylinder cavity, and the hypertonic piston is passed through a through-hole of the hydrostatic front cylinder cover plate and connected to the static force sensor through a connection flange; and
- the static force sensor is connected to the tangential rearward indenter, and the hypertonic sensor barrel is provided on the displacement sensor.

In an embodiment, the tangential disturbance loading cylinder includes a disturbance cylinder barrel;
- two ends of the disturbance cylinder barrel are provided with a disturbance front cylinder cover plate and a disturbance rear cylinder cover plate respectively, and the disturbance front cylinder cover plate is connected to a flange of the disturbance rear cylinder cover plate through connection columns provided along a periphery to fix the disturbance cylinder barrel to form a disturbance loading cylinder body;
- a connection flange that fixes the tangential disturbance loading cylinder to the annular frame is fixed to the connection column, the disturbance cylinder barrel is provided inside with a disturbance piston, the two ends of the disturbance piston are passed out centres of the disturbance front cylinder cover plate and the disturbance rear cylinder cover plate, respectively, and the disturbance piston is connected with a force sensor through a flange of the disturbance piston, and a front end of the force sensor is connected to a disturbance rod.

In an embodiment, the hydraulic system includes a static oil source, a dynamic oil source and a servo valve;
- the static oil source and the dynamic oil source have same structures,
- a hydraulic pump outlet of the static oil source, through a high pressure-resistant oil pipe and the servo valve, is connected to a hypertonic loading cylinder and a tangential hypertonic loading cylinder of the normal dynamic and static combination loading cylinder and the lateral dynamic and static combination loading cylinder respectively; and
- a hydraulic pump outlet of the dynamic oil source, through the high pressure-resistant oil pipe and the servo valve, is connected to a disturbance loading cylinder and a tangential disturbance loading cylinder of the normal dynamic and static combination loading cylinder and the lateral dynamic and static combination loading cylinder, respectively.

In an embodiment, the pore pressure coupling system includes a pore pressure pump;

a water inlet pipeline of the pore pressure pump is provided with an inlet pressure sensor, and the pore pressure pump, an inlet and outlet of the true three-dimensional high-temperature and high pore pressure shear box, an outlet pressure sensor, a rear-pressure valve, and a flowmeter are connected in series through a pressure-resistant water pipe.

A method of using the true three-dimensional dynamic and static combination shear device under high-temperature, high pore pressure and chemical coupling, includes:

step 1: pushing the lateral floating frame away from the annular frame, to make the high-temperature box on the lateral floating frame to be exposed outside the annular frame;

step 2: placing a rock sample into the true three-dimensional high-temperature and high pore pressure shear box, and then placing the true three-dimensional high-temperature and high pore pressure shear box with the rock sample over a normal downward indenter at a center of the high-temperature box;

step 3: installing a deformation sensor, an acoustic emission probe and a microseismic probe in corresponding mounting slots of the true three-dimensional high-temperature and high pore pressure shear box, and then connecting a pressure-resistant water pipe line of the pore pressure system to the true three-dimensional high-temperature and high pore pressure shear box, and then placing a normal upward indenter on a top surface of the true three-dimensional high-temperature and high pore pressure shear box, so that a centre connection line of the normal upward indenter to the normal downward indenter is perpendicular to a horizontal plane, and closing a top cover plate of the high-temperature box;

step 4: pushing the lateral floating frame into the annular frame, and making the rock sample be at a geometric centre of the annular frame, so that the normal dynamic and static combination loading cylinder fixed in a through-hole of an upper end of the annular frame directly faces to the normal upward indenter, and so that a centre connection line of the tangential hypertonic loading cylinder fixed in a through-hole in a left end of the annular frame to the tangential disturbance loading cylinder fixed in a through-hole in a right end of the annular frame coincides with a tangential centre line of the rock sample;

step 5: starting a static oil source, first applying a normal pre-pressure to the rock sample by applying displacement control to the normal dynamic and static combination loading cylinder, then applying a lateral pre-pressure to the rock sample by applying the displacement control to the lateral dynamic and static combination loading cylinder, and then applying a tangential pre-pressure to the rock sample by applying the displacement control to the tangential hydrostatic loading cylinder;

step 6: starting the high-temperature box and presetting a target temperature, so that a temperature in the high-temperature box reaches the preset target temperature;

step 7: controlling the normal dynamic and static combination loading cylinder and the lateral dynamic and static combination loading cylinder by a stress control method, so that a normal stress $\sigma_n$ of the rock sample reaches a target value $\sigma_{n1}$ and a lateral stress $\sigma_p$ reaches a target value $\sigma_{p1}$, and controlling the tangential hydrostatic loading cylinder by the stress control method, to apply force loading at a constant loading rate, so that a tangential stress $\tau$ of the rock sample reaches a target value $\tau_1$;

step 8: starting the pore pressure coupling system, and presetting a target pore pressure water pressure $\sigma_w$ so that the pore pressure water pressure reaches a preset target value;

step 9: starting a dynamic oil source, controlling the normal dynamic and static combination loading cylinder and a disturbance cylinder of the lateral dynamic and static combination loading cylinder by the stress control method, to apply a preset normal disturbance load $\Delta\sigma_n$ and a lateral disturbance load $\Delta\sigma_p$ on the rock sample; when a tangential stress $\tau$ of the rock sample reaches the target value $\tau_1$, and then controlling the tangential disturbance loading cylinder through the stress control method, to apply a tangential disturbance load $\Delta\tau$ to the rock sample, to maintain the hypertonic pressure unchanged;

after the tangential disturbance load $\Delta\tau$ is applied for a preset number of cycles T, removing the tangential disturbance load $\Delta\tau_1$, and then controlling the tangential hydrostatic loading cylinder by the stress control method, to apply force loading at the constant loading rate, so that the tangential stress of the rock sample reaches a second target value $\tau_2$ from $\tau_1$, and then controlling the tangential disturbance loading cylinder through the stress control method, to apply the tangential disturbance load $\Delta\tau$ to the rock sample, to maintain the hypertonic unchanged;

after the tangential disturbance load $\Delta\tau$ is applied for the preset number of cycles T, removing the tangential disturbance load $\Delta\tau_1$, then controlling the tangential hydrostatic loading cylinder by the stress control method, so that the tangential stress of the rock sample reaches a third target value $\tau_3$ from $\tau_2$, and so on until the rock sample is damaged; and step 10: connecting an interface of a computer to a force sensor of each loading cylinder, and a displacement sensor and the deformation sensor in each direction, and feeding a real-time detection signal back to the computer, and recording, by the computer, a force value and displacement and deformation data of the rock sample in each direction in a test process, and collecting acoustic information of the rock sample in the test process by the acoustic emission probe and the microvibration probe in real-time.

Beneficial effects of the present application:

The present application has the following significant advantages over the related art, firstly, the present application for the first time realizes the multi-directional disturbance shear test of the rock structural plane under the true triaxial stress conditions, which can simultaneously apply the dynamic and static combination load to the normal, lateral and tangential directions of the rock structural plane, while further improving on the loading cylinder by combining the static and disturbance cylinders together, thereby realizing that the disturbance load is applied on the same side of the static load; secondly, the present application realizes a complex stress environment with high-temperature, hypertonic water pressure and chemical corrosion coupling. The permeability water pressure can reach a high level of 20 MPa, and the permeability module pipeline adopts Hastelloy material to realize chemical corrosion of strong acid and alkaline solution. The present application provides practical hardware conditions for the study of characteristics of the rock structural plane shear under complex environment with multi-factor coupling, which is of great significance to the research field of rock mechanics.

1—annular frame, 2—frame base, 3—lateral horizontal support platform, 4—lateral floating frame, 5—normal dynamic and static combination loading cylinder, 501—dynamic and static front cylinder cover plate, 502—first cylinder barrel, 503—hypertonic piston, 504—hypertonic transducer, 505—second cylinder barrel, 506—rear cylinder cover plate, 507—disturbance piston, 508—dynamic force sensor, 509—hydrostatic displacement sensor, 510—disturbance displacement sensor, 6—lateral dynamic and static combination loading cylinder, 7—tangential disturbance loading cylinder, 701—hydrostatic front cylinder cover plate, 702—hydrostatic cylinder barrel, 703—hydrostatic piston, 704—connection flange, 705—static force sensor, 706—tangential rearward indenter, 707—displacement sensor, 8—tangential disturbance loading cylinder, 801—front cylinder cover plate, 802—connection flange, 803—disturbance cylinder barrel, 804—rear cylinder cover plate, 805—disturbance piston, 806—force transducer, 807—disturbance rod, 9—high-temperature box, 10—true three-dimensional high-temperature shear box, 11—rock sample, 12—lateral left indenter, 13—lateral right indenter, 14—normal upward indenter, 15—normal downward indenter, 16—static oil source, 17—dynamic oil source, 18—servo valve, 19—pore pressure pump, 20—inlet pressure sensor, 21—outlet pressure sensor, 22—rear pressure valve, 23—flowmeter, 24—slide rail.

DETAILED DESCRIPTION OF THE EMBODIMENTS

The present application is described in further detail below in connection with the accompanying drawings and embodiments.

Figure 1:
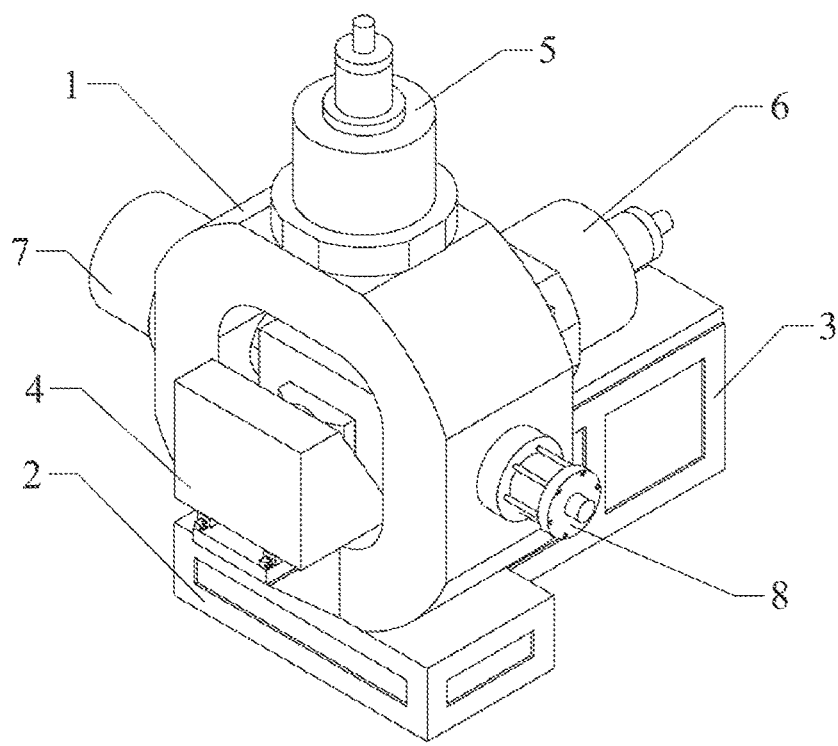
FIG. 1 is a three-dimensional structural schematic diagram of the true three-dimensional dynamic and static combination shear device under high-temperature, high pore pressure and chemical coupling of the present application.
Figure 2:
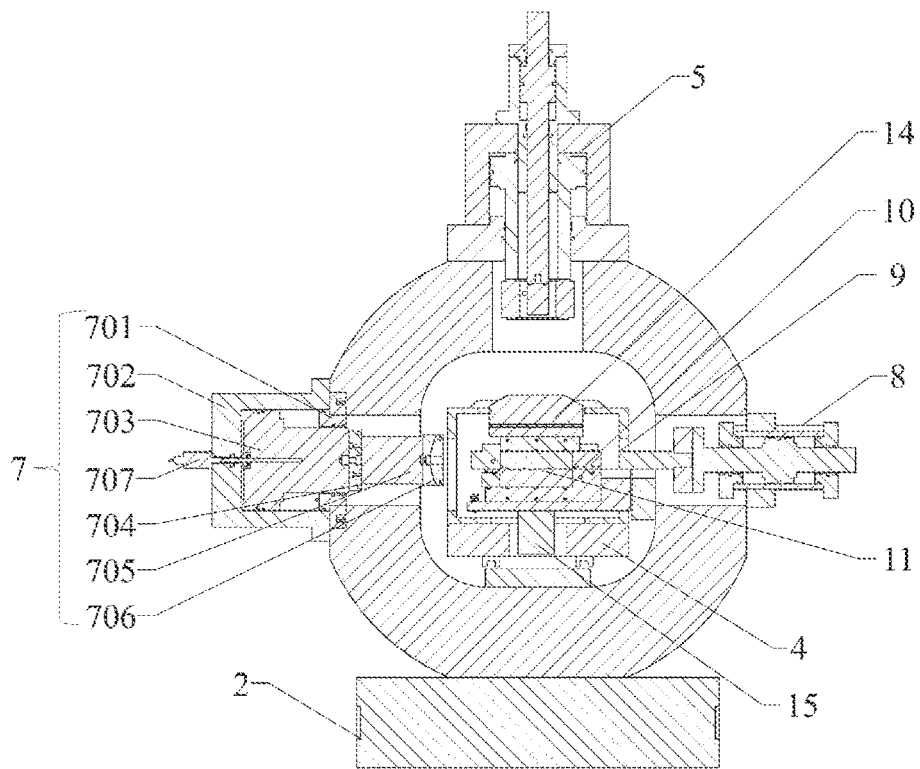
FIG. 2 is a front sectional view of the true three-dimensional dynamic and static combination shear device under high-temperature, high pore pressure and chemical coupling of the present application.
Figure 3:
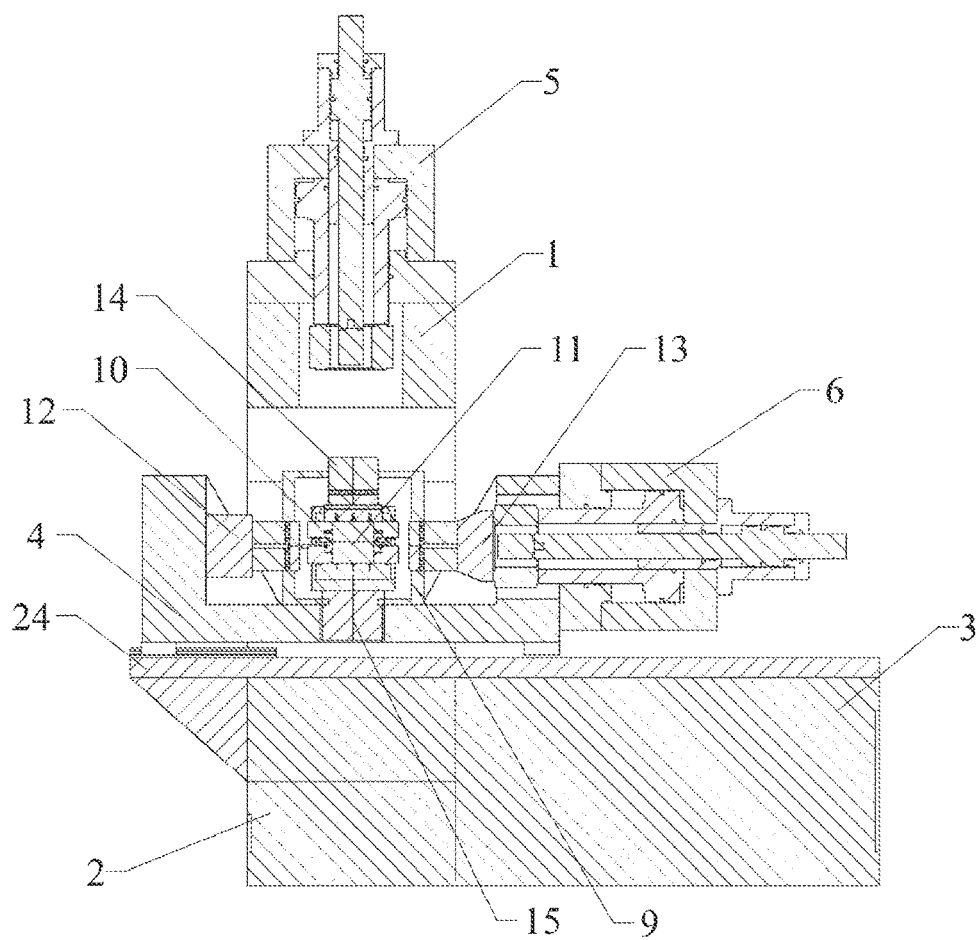
FIG. 3 is a side sectional view of the true three-dimensional dynamic and static combination shear device under high-temperature, high pore pressure and chemical coupling of the present application.
Figure 4:
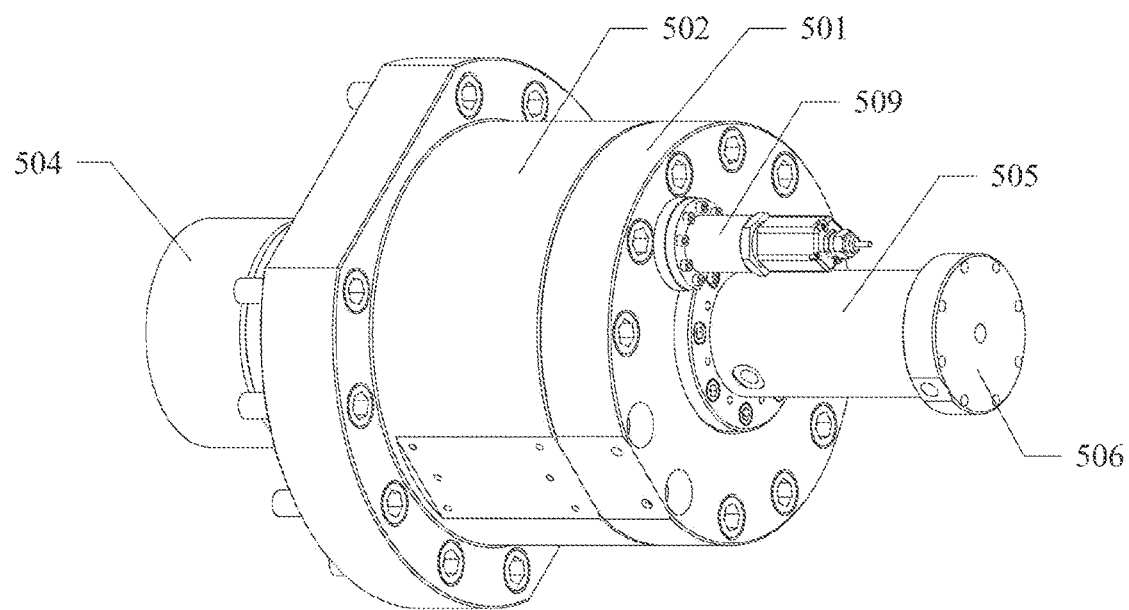
FIG. 4 is a structural view of the normal dynamic and static combination loading cylinder and lateral dynamic and static combination loading cylinder of the true three-dimensional dynamic and static combination shear device under high-temperature, high pore pressure and chemical coupling of the present application.
Figure 5:
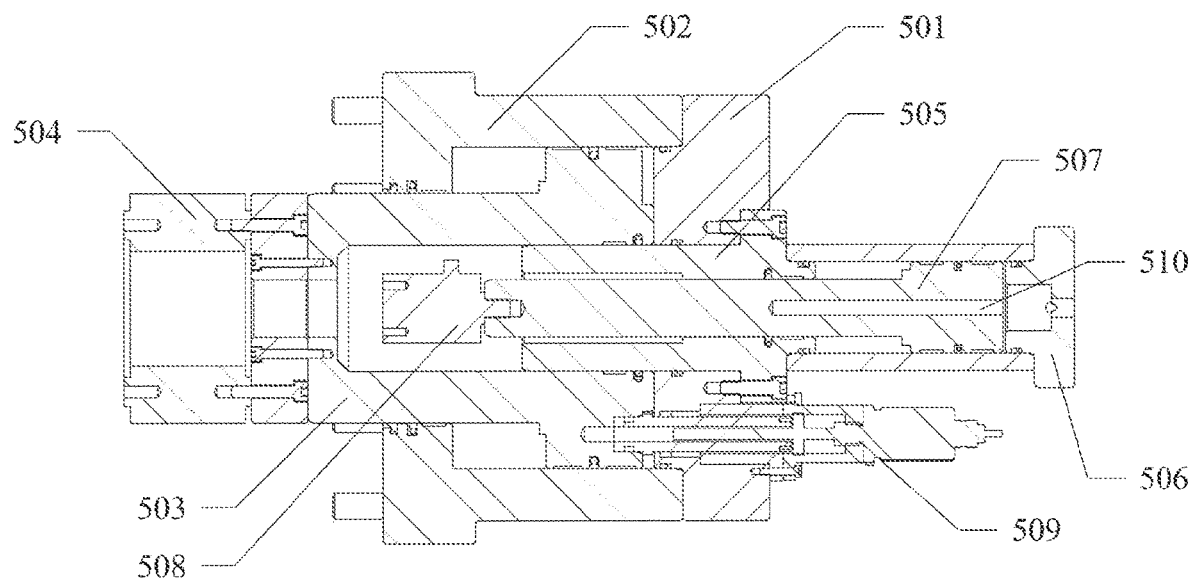
FIG. 5 is a sectional view of the normal dynamic and static combination loading cylinder and lateral dynamic and static combination loading cylinder of the true three-dimensional dynamic and static combination shear device under high-temperature, high pore pressure and chemical coupling of the present application.
Figure 6:
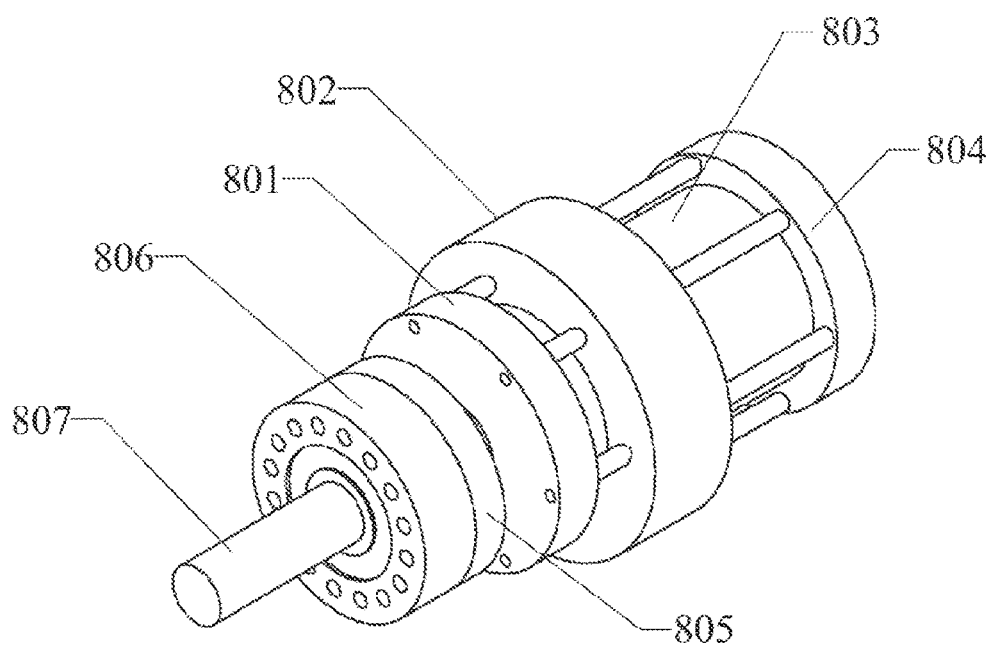
FIG. 6 is a structural view of the tangential disturbance loading cylinder of the true true three-dimensional dynamic and static combination shear device under high-temperature, high pore pressure and chemical coupling of the present application.
Figure 7:
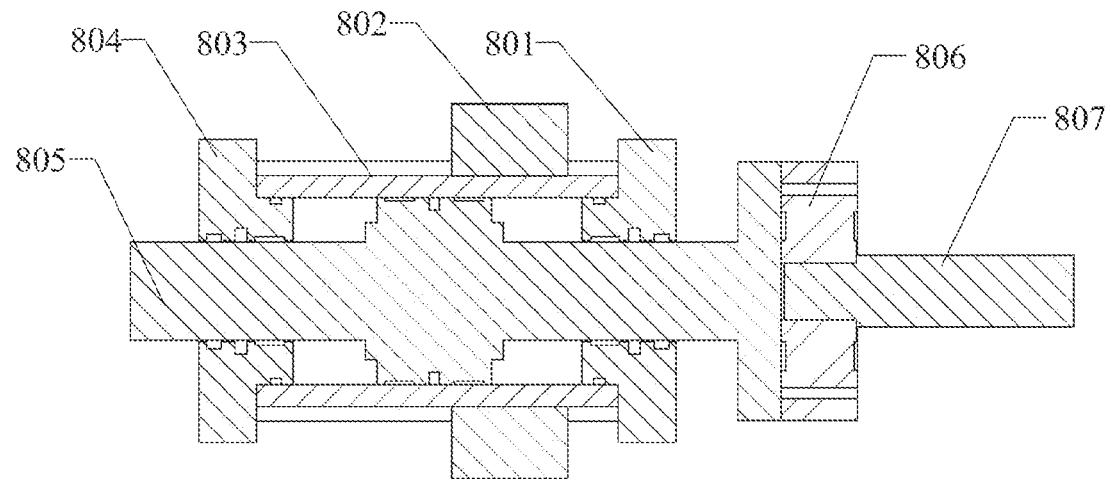
FIG. 7 is a sectional view of the tangential disturbance loading cylinder of the true three-dimensional dynamic and static combination shear device under high-temperature, high pore pressure and chemical coupling of the present application.
Figure 8:
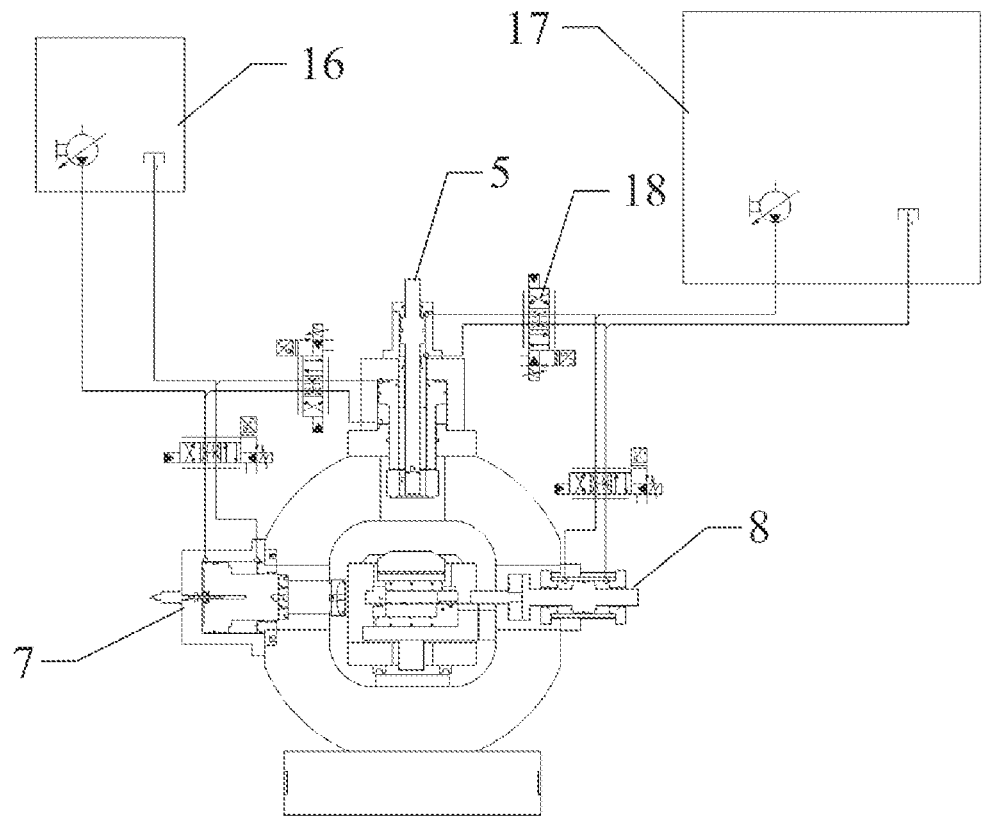
FIG. 8 is a front view hydraulic schematic diagram of the true three-dimensional dynamic and static combination shear device under high-temperature, high pore pressure and chemical coupling of the present application.
Figure 9:
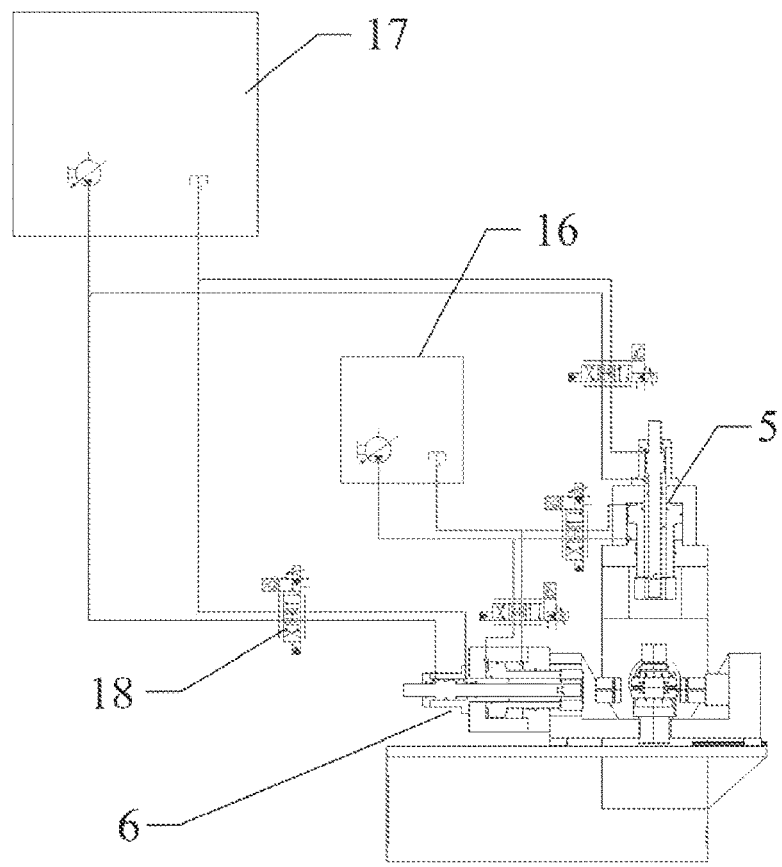
FIG. 9 is a side view hydraulic schematic diagram of the true three-dimensional dynamic and static combination shear device under high-temperature, high pore pressure and chemical coupling of the present application.
Figure 10:
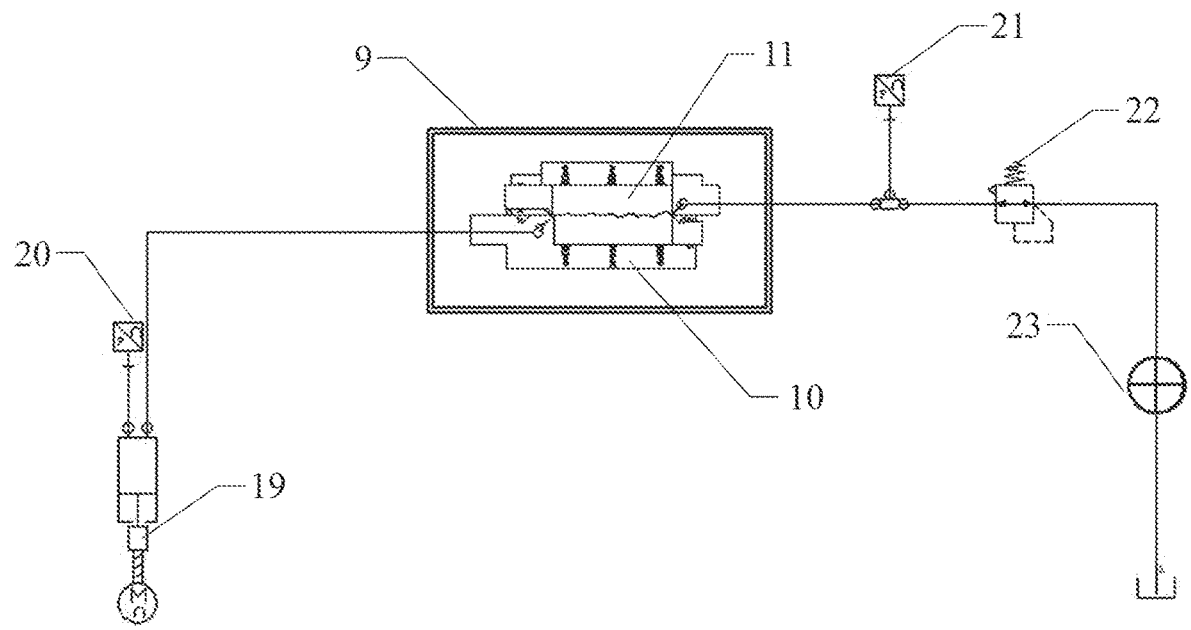
FIG. 10 is a pore pressure schematic diagram of the true three-dimensional dynamic and static combination shear device under high-temperature, high pore pressure and chemical coupling of the present application.

As shown in FIGS. 1 to 10, a true three-dimensional dynamic and static combination shear device under high-temperature, high pore pressure and chemical coupling includes a hydraulic system, a pore pressure coupling system and a main body loading system; the main body loading system is connected to the hydraulic system and the pore pressure coupling system, and is controlled through the hydraulic system to load a sample; and the pore pressure coupling system is configured to provide water for a true three-dimensional high-temperature and high pore pressure shear box 10 of the main body loading system to complete a high-temperature, high pore pressure and chemical coupling of the sample.

the main body loading system includes a frame base 2; a rear end of the frame base 2 is provided with a lateral horizontal support platform 3, and an annular frame 1 is fixed to an upper surface of the frame base 2 through a bolt; a lower surface of an inner cavity of the annular frame 1 is flush with an upper surface of the lateral horizontal support platform 3, and the lower surface of the inner cavity of the annular frame 1 is provided with a slide rail 24 extending to the lateral horizontal support platform 3; a lateral floating frame 4 is provided on the slide rail 24 through a slider, and a normal dynamic and static combination loading cylinder 5 is fixed in a through-hole in an upper portion of the annular frame 1; a tangential disturbance loading cylinder 8 is fixed in a through-hole in a front-side of the annular frame 1 and a tangential hydrostatic loading cylinder 7 is fixed in a through-hole in a rear-side of the annular frame 1; the lateral floating frame 4 is of an U-type integrated frame, and a lateral dynamic and static combination loading cylinder 6 is fixed in a through-hole in a right end of the lateral floating frame 4, and a left end of the lateral dynamic and static combination loading cylinder 6 is connected to a lateral right indenter 13; a normal downward indenter 15 is fixed in a vertical through-hole in a middle of the lateral floating frame 4, a lateral left indenter 12 facing to the lateral right indenter 13 is fixed to a left end of the lateral floating frame 4, and the high-temperature box 9 is placed in the middle of the lateral floating frame 4, and the high-temperature box 9 is provided with through-holes in a middle of six surfaces, such as a top, bottom, front, rear, left and right surface; the normal downward indenter 15 is passed through a through-hole at a bottom of the high-temperature box 9, the lateral left indenter 12 is passed through a through-hole at the left surface of the high-temperature box 9, and the lateral right indenter 13 is passed through a through-hole at the right surface of the high-temperature box 9;

a tangential rearward indenter 706 of the tangential hydrostatic loading cylinder 7 is passed through a through-hole at the front surface of the high-temperature box 9 and a disturbance rod 807 of the tangential disturbance loading cylinder 8 is passed through a through-hole at the rear surface of the high-temperature box 9; and the true three-dimensional high-temperature and high pore pressure shear box 10 is in the high-temperature box 9 and is provided over the normal downward indenter 15 inside the high-temperature box 9; and a normal upward indenter 14 is passed through a through-hole at the top surface of the high-temperature box 9 and then provided on a top of true three-dimensional high-temperature and high pore pressure shear box 10.

The normal dynamic and static combination loading cylinder 5 and the lateral dynamic and static combination loading cylinder 6 have same structures, and both include a dynamic and static front cylinder cover plate 501, and the dynamic and static front cylinder cover plate 501 is fixed to a first cylinder barrel 502 to form a hydrostatic cylinder cavity; a hydrostatic piston 503 is provided inside the hydrostatic cylinder cavity to form a hydrostatic loading cylinder, a static force sensor 504 is connected to a front end of the hydrostatic piston 503; a front end of a second cylinder barrel 505 is extended into the first cylinder barrel 502 and is fixed to the first cylinder barrel 502; a rear cylinder cover plate 506 is fixed to a rear end of the second cylinder barrel 505 to form a disturbance cylinder cavity; a front end of a disturbance piston 507 is passed through the second cylinder barrel 505 and an inside of the hydrostatic piston 503, and then provided in the second cylinder barrel 505 to form a disturbance loading cylinder; a dynamic force sensor 508 is connected to the front end of the disturbance piston 507; and a hydrostatic displacement sensor 509 is provided on the dynamic and static front cylinder cover plate 501 and a disturbance displacement sensor 510 is provided on the disturbance piston 507.

The tangential hydrostatic loading cylinder 7 includes a hydrostatic front cylinder cover plate 701; the hydrostatic front cylinder cover plate 701 is fixed to a hydrostatic cylinder barrel 702 to form a tangential hydrostatic loading cylinder cavity; the hypertonic piston 703 is provided in the tangential hydrostatic loading cylinder cavity, and the hypertonic piston 703 is passed through a through-hole of the hydrostatic front cylinder cover plate 701 and connected to the static force sensor 705 through a connection flange 704; and the static force sensor 705 is connected to the tangential rearward indenter 706, and the hypertonic sensor barrel 702 is provided on the displacement sensor 707.

The tangential disturbance loading cylinder 8 includes a disturbance cylinder barrel 803; two ends of the disturbance cylinder barrel 803 are provided with a disturbance front cylinder cover plate 801 and a disturbance rear cylinder cover plate 804 respectively, and the disturbance front cylinder cover plate 801 is connected to a flange of the disturbance rear cylinder cover plate 804 through connection columns provided along a periphery to fix the disturbance cylinder barrel 803 to form a disturbance loading cylinder body; a connection flange 802 that fixes the tangential disturbance loading cylinder 8 to the annular frame is fixed to the connection column, the disturbance cylinder barrel 803 is provided inside with a disturbance piston 805, the two ends of the disturbance piston 805 are passed out centres of the disturbance front cylinder cover plate 801 and the disturbance rear cylinder cover plate 804, respectively, and the disturbance piston 805 is connected with a force sensor 806 through a flange of the disturbance piston, and a front end of the force sensor 806 is connected to a disturbance rod 807.

The hydraulic system includes a static oil source 16, a dynamic oil source 17 and six servo valve 18; the static oil source 16 and the dynamic oil source 17 have same structures, a hydraulic pump outlet of the static oil source 16, through a high pressure-resistant oil pipe and three servo valves 18, is connected to a hypertonic loading cylinder and a tangential hypertonic loading cylinder 7 of the normal dynamic and static combination loading cylinder 5 and the lateral dynamic and static combination loading cylinder 6 respectively; and a hydraulic pump outlet of the dynamic oil source 17, through the high pressure-resistant oil pipe and three servo valves 18, is connected to a disturbance loading cylinder and a tangential disturbance loading cylinder 8 of the normal dynamic and static combination loading cylinder 5 and the lateral dynamic and static combination loading cylinder 6, respectively. Through the synergistic effect of the hydraulic pump and the servo valve 18, it is ensured that the actuator high-frequency movement, to ensure that the completion of the constant normal stiffness test; a pressure control of the static oil source 16 is controlled by using the servo, how much pressure is preset, then all preset pressure is output, the effect of overflow will not produced, that is, all the work done by the oil pump motor is converted to the output pressure, there is no excess energy is converted to heat, the oil tank of the static oil source 16 is 20 L, and the oil tank of the dynamic oil source 17 is 100 L.

The pore pressure coupling system includes a pore pressure pump 19, an inlet and outlet pressure sensor 20, an outlet pressure sensor 21, a rear pressure valve 22, a flowmeter 23, a pressure-resistant water pipe, the inlet pressure sensor 20 is provided on a water inlet pipe of the pore pressure pump 19. The pore pressure pump 19, the inlet and outlet of the true three-dimensional high-temperature and high pore pressure shear box 10, an outlet pressure sensor 1, a rear pressure valve 22 and the flowmeter 23 are connected in series through a pressure-resistant water pipe. During the device, the pore pressure water is introduced from the inlet into a lower shear box of the true three-dimensional high-temperature and high pore pressure shear box 10, and then flows into along a shear direction of a structural plane shear surface of the rock, and then flows out of the outlet through the pressure-resistant water pipe connected to an upper shear box. The pore pressure water pressure is designed to be a maximum pressure of 20 MPa. The pressure-resistant water pipe is made of Hastelloy material, which is corrosion-resistant and thermally stable, which allows the pore pressure line to work in a high temperature, high pore pressure and high corrosion environment.

The high-temperature box 9 is a constant temperature box, the rock sample 11 in the shear box 10 is heated by ceramic radiation heating.

A method of using the true three-dimensional dynamic and static combination shear device under high-temperature, high pore pressure and chemical coupling, includes:

step 1: pushing the lateral floating frame 4 away from the annular frame 1, to make the high-temperature box 9 on the lateral floating frame 4 to be exposed outside the annular frame 1;

step 2: placing a rock sample 11 into the true three-dimensional high-temperature and high pore pressure shear box 10, and then placing the true three-dimensional high-temperature and high pore pressure shear box 10 with the rock sample 11 over a normal downward indenter 15 at a center of the high-temperature box 9;

step 3: installing a deformation sensor, an acoustic emission probe and a microseismic probe in corresponding mounting slots of the true three-dimensional high-temperature and high pore pressure shear box 10, and then connecting a pressure-resistant water pipe line of the pore pressure system to the true three-dimensional high-temperature and high pore pressure shear box 10, and then placing a normal upward indenter 14 on a top surface of the true three-dimensional high-temperature and high pore pressure shear box 10, so that a centre connection line of the normal upward indenter 14 to the normal downward indenter 15 is perpendicular to a horizontal plane, and closing a top cover plate of the high-temperature box 9;

step 4: pushing the lateral floating frame 4 into the annular frame 1, and making the rock sample 11 be at a geometric centre of the annular frame 1, so that the normal dynamic and static combination loading cylinder 5 fixed in a through-hole of an upper end of the annular frame 1 directly faces to the normal upward indenter 14, and so that a centre connection line of the tangential hypertonic loading cylinder 7 fixed in a through-hole in a left end of the annular frame 1 to the tangential disturbance loading cylinder 8 fixed in a through-hole in a right end of the annular frame 1 coincides with a tangential centre line of the rock sample 11;

step 5: starting a static oil source 17, first applying a normal pre-pressure to the rock sample 11 by applying displacement control to the normal dynamic and static combination loading cylinder 5, then applying a lateral pre-pressure to the rock sample 11 by applying the displacement control to the lateral dynamic and static combination loading cylinder 6, and then applying a tangential pre-pressure to the rock sample 11 by applying the displacement control to the tangential hydrostatic loading cylinder 7;

step 6: starting the high-temperature box 9 and presetting a target temperature, so that a temperature in the high-temperature box 9 reaches the preset target temperature;

step 7: controlling the normal dynamic and static combination loading cylinder 5 and the lateral dynamic and static combination loading cylinder 6 by a stress control method, so that a normal stress $\sigma_n$ of the rock sample 11 reaches a target value $\sigma_{n1}$ and a lateral stress $\sigma_p$ reaches a target value $\sigma_{p1}$, and controlling the tangential hydrostatic loading cylinder 7 by the stress control method, to apply force loading at a constant loading rate, so that a tangential stress $\tau$ of the rock sample 11 reaches a target value $\tau_1$;

step 8: starting the pore pressure coupling system, and presetting a target pore pressure water pressure $\sigma_w$, so that the pore pressure water pressure reaches a preset target value;

step 9: starting a dynamic oil source 17, controlling the normal dynamic and static combination loading cylinder 5 and a disturbance cylinder of the lateral dynamic and static combination loading cylinder 6 by the stress control method, to apply a preset normal disturbance load $\Delta\sigma_n$ and a lateral disturbance load $\Delta\sigma_p$ on the rock sample 11; when a tangential stress $\tau$ of the rock sample 11 reaches the target value $\tau_1$, and then controlling the tangential disturbance loading cylinder 8 through the stress control method, to apply a tangential disturbance load $\Delta\tau$ to the rock sample 11, to maintain the hypertonic pressure unchanged;

after the tangential disturbance load $\Delta\tau$ is applied for a preset number of cycles T, removing the tangential disturbance load $\Delta\tau_1$, and then controlling the tangential hydrostatic loading cylinder 7 by the stress control method, to apply force loading at the constant loading rate, so that the tangential stress of the rock sample 11 reaches a second target value $\tau_2$ from $\tau_1$, and then controlling the tangential disturbance loading cylinder 8 through the stress control method, to apply the tangential disturbance load $\Delta\tau$ to the rock sample 11, to maintain the hypertonic unchanged;

after the tangential disturbance load $\Delta\tau$ is applied for the preset number of cycles T, removing the tangential disturbance load $\Delta\tau_1$, then controlling the tangential hydrostatic loading cylinder 7 by the stress control method, so that the tangential stress of the rock sample 11 reaches a third target value $\tau_3$ from $\tau_2$, and so on until the rock sample 11 is damaged; and step 10: connecting an interface of a computer to a force sensor of each loading cylinder, and a displacement sensor and the deformation sensor in each direction, and feeding a real-time detection signal back to the computer, and recording, by the computer, a force value and displacement and deformation data of the rock sample in each direction in a test process, and collecting acoustic information of the rock sample in the test process by the acoustic emission probe and the microvibration probe in real-time.

The invention claimed is:

1. A true three-dimensional dynamic and static combination shear device under high-temperature, high pore pressure and chemical coupling, comprising:

a hydraulic system, a pore pressure coupling system and a main body loading system;

wherein the main body loading system is connected to the hydraulic system and the pore pressure coupling system, and is controlled through the hydraulic system to load a sample; and the pore pressure coupling system is configured to provide water for a true three-dimensional high-temperature, high pore pressure and chemical coupling shear box of the main body loading system to complete a high-temperature, high pore pressure and chemical coupling of the sample;

wherein the main body loading system comprises a frame base;

wherein a rear end of the frame base is provided with a lateral horizontal support platform, and an annular frame is fixed to an upper surface of the frame base through a bolt;

a lower surface of an inner cavity of the annular frame is flush with an upper surface of the lateral horizontal support platform, and the lower surface of the inner cavity of the annular frame is provided with a slide rail extending to the lateral horizontal support platform;

a lateral floating frame is provided on the slide rail through a slider, and a normal dynamic and static combination loading cylinder is fixed in a through-hole in an upper portion of the annular frame;

a tangential disturbance loading cylinder is fixed in a through-hole in a front-side of the annular frame and a tangential hydrostatic loading cylinder is fixed in a through-hole in a rear-side of the annular frame;

the lateral floating frame is of an U-type integrated frame, and a lateral dynamic and static combination loading cylinder is fixed in a through-hole in a right end of the lateral floating frame, and a left end of the lateral dynamic and static combination loading cylinder is connected to a lateral right indenter;

a normal downward indenter is fixed in a vertical through-hole in a middle of the lateral floating frame, a lateral left indenter facing to the lateral right indenter is fixed to a left end of the lateral floating frame, and the high-temperature box is placed in the middle of the lateral floating frame, and the high-temperature box is provided with through-holes in a middle of six surfaces, such as a top, bottom, front, rear, left and right surface;

the normal downward indenter is passed through a through-hole at a bottom of the high-temperature box, the lateral left indenter is passed through a through-hole at the left surface of the high-temperature box, and the lateral right indenter is passed through a through-hole at the right surface of the high-temperature box;

a tangential rearward indenter of the tangential hydrostatic loading cylinder is passed through a through-hole at the front surface of the high-temperature box and a disturbance rod of the tangential disturbance loading cylinder is passed through a through-hole at the rear surface of the high-temperature box; and the true three-dimensional high-temperature shear box is in the high-temperature box and is provided over the normal downward indenter inside the high-temperature box; and a normal upward indenter is passed through a through-hole at the top surface of the high-temperature box and then provided on a top of the true three-dimensional high-temperature shear box.

2. The true three-dimensional dynamic and static combination shear device under high-temperature, high pore pressure and chemical coupling according to claim 1, wherein the normal dynamic and static combination loading cylinder and the lateral dynamic and static combination loading cylinder have same structures, and both comprise a dynamic and static front cylinder cover plate, and the dynamic and static front cylinder cover plate is fixed to a first cylinder barrel to form a hydrostatic cylinder cavity;

a hydrostatic piston is provided inside the hydrostatic cylinder cavity to form a hydrostatic loading cylinder, a static force sensor is connected to a front end of the hydrostatic piston; a front end of a second cylinder barrel is extended into the first cylinder barrel and is fixed to the first cylinder barrel;

a rear cylinder cover plate is fixed to a rear end of the second cylinder barrel to form a disturbance cylinder cavity; a front end of a disturbance piston is passed through the second cylinder barrel and an inside of the hydrostatic piston, and then provided in the second cylinder barrel to form a disturbance loading cylinder;

a dynamic force sensor is connected to the front end of the disturbance piston; and a hydrostatic displacement sensor is provided on the dynamic and static front cylinder cover plate and a disturbance displacement sensor is provided on the disturbance piston.

3. The true three-dimensional dynamic and static combination shear device under high-temperature, high pore pressure and chemical coupling according to claim 1, wherein the tangential hydrostatic loading cylinder comprises a hydrostatic front cylinder cover plate;

the hydrostatic front cylinder cover plate is fixed to a hydrostatic cylinder barrel to form a tangential hydrostatic loading cylinder cavity;

the hypertonic piston is provided in the tangential hydrostatic loading cylinder cavity, and the hypertonic piston is passed through a through-hole of the hydrostatic front cylinder cover plate and connected to the static force sensor through a connection flange; and the static force sensor is connected to the tangential rearward indenter, and the hypertonic sensor barrel is provided on the displacement sensor.

4. The true three-dimensional dynamic and static combination shear device under high-temperature, high pore pressure and chemical coupling according to claim 1, wherein the tangential disturbance loading cylinder comprises a disturbance cylinder barrel;

two ends of the disturbance cylinder barrel are provided with a disturbance front cylinder cover plate and a disturbance rear cylinder cover plate respectively, and the disturbance front cylinder cover plate is connected to a flange of the disturbance rear cylinder cover plate through connection columns provided along a periphery to fix the disturbance cylinder barrel to form a disturbance loading cylinder body;

a connection flange that fixes the tangential disturbance loading cylinder to the annular frame is fixed to the connection column, the disturbance cylinder barrel is provided inside with a disturbance piston, the two ends of the disturbance piston are passed out centres of the disturbance front cylinder cover plate and the disturbance rear cylinder cover plate, respectively, and the disturbance piston is connected with a force sensor through a flange of the disturbance piston, and a front end of the force sensor is connected to a disturbance rod.

5. The true three-dimensional dynamic and static combination shear device under high-temperature, high pore pressure and chemical coupling according to claim 1, wherein the hydraulic system comprises a static oil source, a dynamic oil source and a servo valve;

the static oil source and the dynamic oil source have same structures, a hydraulic pump outlet of the static oil source, through a high pressure-resistant oil pipe and the servo valve, is connected to a hypertonic loading cylinder and a tangential hypertonic loading cylinder of the normal dynamic and static combination loading cylinder and the lateral dynamic and static combination loading cylinder respectively; and a hydraulic pump outlet of the dynamic oil source, through the high pressure-resistant oil pipe and the servo valve, is connected to a disturbance loading cylinder and a tangential disturbance loading cylinder of the normal dynamic and static combination loading cylinder and the lateral dynamic and static combination loading cylinder, respectively.

6. The true three-dimensional dynamic and static combination shear device under high-temperature, high pore pressure and chemical coupling according to claim 1, wherein the pore pressure coupling system comprises a pore pressure pump;

a water inlet pipeline of the pore pressure pump is provided with an inlet pressure sensor, and the pore pressure pump, an inlet and outlet of the true three-dimensional high-temperature and high pore pressure shear box, an outlet pressure sensor, a rear pressure valve, and a flowmeter are connected in series through a pressure-resistant water pipe.

7. A method for using the true three-dimensional dynamic and static combination shear device under high-temperature, high pore pressure and chemical coupling according to claim 1, comprising:

step 1: pushing the lateral floating frame away from the annular frame, to make the high-temperature box on the lateral floating frame to be exposed outside the annular frame;

step 2: placing a rock sample into the true three-dimensional high-temperature shear box, and then placing the true three-dimensional high-temperature shear box with the rock sample over a normal downward indenter at a center of the high-temperature box;

step 3: installing a deformation sensor, an acoustic emission probe and a microseismic probe in corresponding mounting slots of the true three-dimensional high-temperature shear box, and then connecting a pressure-resistant water pipe line of the pore pressure system to the true three-dimensional high-temperature shear box, and then placing a normal upward indenter on a top surface of the true three-dimensional high-temperature shear box, so that a center connection line of the normal upward indenter to the normal downward indenter is perpendicular to a horizontal plane, and closing a top cover plate of the high-temperature box;

step 4: pushing the lateral floating frame into the annular frame, and making the rock sample be at a geometric center of the annular frame, so that the normal dynamic and static combination loading cylinder fixed in a through-hole of an upper end of the annular frame directly faces to the normal upward indenter, and so that a center connection line of the tangential hypertonic loading cylinder fixed in a through-hole in a left end of the annular frame to the tangential disturbance loading cylinder fixed in a through-hole in a right end of the annular frame coincides with a tangential center line of the rock sample;

step 5: starting a static oil source, first applying a normal pre-pressure to the rock sample by applying displacement control to the normal dynamic and static combination loading cylinder, then applying a lateral pre-pressure to the rock sample by applying the displacement control to the lateral dynamic and static combination loading cylinder, and then applying a tangential pre-pressure to the rock sample by applying the displacement control to the tangential hydrostatic loading cylinder;

step 6: starting the high-temperature box and presetting a target temperature, so that a temperature in the high-temperature box reaches the preset target temperature;

step 7: controlling the normal dynamic and static combination loading cylinder and the lateral dynamic and static combination loading cylinder by a stress control method, so that a normal stress $\sigma_n$ of the rock sample reaches a target value $\sigma_{n1}$ and a lateral stress $\sigma_p$ reaches a target value $\sigma_{p1}$, and controlling the tangential hydrostatic loading cylinder by the stress control method, to apply force loading at a constant loading rate, so that a tangential stress $\tau$ of the rock sample reaches a target value $\tau_1$;

step 8: starting the pore pressure coupling system, and presetting a target pore pressure water pressure $\sigma_w$, so that the pore pressure reaches a preset target value;

step 9: starting a dynamic oil source, controlling the normal dynamic and static combination loading cylinder and a disturbance cylinder of the lateral dynamic and static combination loading cylinder by the stress control method, to apply a preset normal disturbance load $\Delta\sigma_n$ and a lateral disturbance load $\Delta\sigma_p$ on the rock sample; when a tangential stress $\tau$ of the rock sample reaches the target value $\tau_1$, and then controlling the tangential disturbance loading cylinder through the stress control method, to apply a tangential disturbance load $\Delta\tau$ to the rock sample, to maintain the pore pressure unchanged;

after the tangential disturbance load $\Delta\tau$ is applied for a preset number of cycles T, removing the tangential disturbance load $\Delta\tau_1$, and then controlling the tangential hydrostatic loading cylinder by the stress control method, to apply force loading at the constant loading rate, so that the tangential stress of the rock sample reaches a second target value $\tau_2$ from $\tau_1$, and then controlling the tangential disturbance loading cylinder through the stress control method, to apply the tangential disturbance load $\Delta\tau$ to the rock sample, to maintain the hypertonic unchanged;

after the tangential disturbance load $\Delta\tau$ is applied for the preset number of cycles T, removing the tangential disturbance load $\Delta\tau_1$, then controlling the tangential hydrostatic loading cylinder by the stress control method, so that the tangential stress of the rock sample reaches a third target value $\tau_3$ from $\tau_2$, and so on until the rock sample is damaged; and step 10: connecting an interface of a computer to a force sensor of each loading cylinder, and a displacement sensor and the deformation sensor in each direction, and feeding a real-time detection signal back to the computer, and recording, by the computer, a force value and displacement and deformation data of the rock sample in each direction in a test process, and collecting acoustic information of the rock sample in the test process by the acoustic emission probe and the microvibration probe in real-time.

* * * * *